United States Patent [19]

Holman, III et al.

[11] Patent Number: 6,037,085
[45] Date of Patent: *Mar. 14, 2000

[54] PHOTORESISTS AND METHOD FOR MAKING PRINTING PLATES

[75] Inventors: Bruce Holman, III, Milwaukee; Jeffrey G. Zaloom, Waukesha; Peiguang Zhou, Racine; Larry Sharkozy, Racine; Merlin L. Mulvey, Racine, all of Wis.

[73] Assignee: Printing Development Inc., Racine, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/666,169

[22] Filed: Jun. 19, 1996

[51] Int. Cl.$^7$ ................................. B41N 1/04; G03C 1/77
[52] U.S. Cl. .................. 430/18; 430/197; 430/270.1; 430/277.1; 430/278.1; 101/457
[58] Field of Search ..................... 430/194, 196, 430/197, 270.1, 326, 944, 945, 195, 287.1, 18, 277.1, 278.1, 457

[56] References Cited

U.S. PATENT DOCUMENTS

| | | | |
|---|---|---|---|
| 2,692,826 | 10/1954 | Neugebauer et al. | 430/302 |
| 2,760,863 | 8/1956 | Plambeck, Jr. | 95/5.6 |
| 3,002,003 | 9/1961 | Merrill et al. | 260/346.3 |
| 3,929,489 | 12/1975 | Arcesi et al. | 430/278.1 |
| 4,722,883 | 2/1988 | Koibuchi et al. | 430/323 |
| 4,732,840 | 3/1988 | Hasegawa | 430/197 X |
| 5,219,700 | 6/1993 | Nakai et al. | 430/194 X |
| 5,278,023 | 1/1994 | Bills et al. | 430/270.1 X |
| 5,372,915 | 12/1994 | Haley et al. | 430/302 |
| 5,478,614 | 12/1995 | Morgan et al. | 428/29 |
| 5,691,098 | 11/1997 | Busman et al. | 430/158 |
| 5,705,309 | 1/1998 | West et al. | 430/167 |

FOREIGN PATENT DOCUMENTS

| | | | |
|---|---|---|---|
| 2171472 | 1/1996 | Canada | G03F 7/09 |
| 0 302 827 | 2/1989 | European Pat. Off. | G03F 7/16 |

OTHER PUBLICATIONS

"Infrared Absorbing Dyes", Masaru Matsuoka, Topics in Applied Chemistry, Plenum Press, 1990, pp. 1–3 and 7–33.

Cai et al, "Conducting Polymers as Deep–UV and Electron Beam Resists: Direct Production of Micrometer Scale Conducting Structures from Poly(3–octylthiophene)", J. Molec. Electronics vol. 7, 1991, pp. 63–68.

European Searcvh Report dated Oct. 13, 1997 for Appln. No. 97109966.8.

Brochure of Printing Developments, Inc, No. 175, 1993.

"CTP Vendors Ask: Which Plate Choice", Graphics Arts Monthly, Feb. 1996.

PDI Printing Developments Brochure, vol. 2 No. 1.

"Printing Perfection" Product Brochure of PDI.

Cai et al, "Development of Highly Efficient Deep–UV and Electrom Beam Mediated Cross–Linkers: Synthesis and Photolysis of Bis(perfluorophenyl Azides", Chem. Mat. vol. 6, No. 10, 1994, pp. 1822–1829.

*Primary Examiner*—Bernard Codd
*Attorney, Agent, or Firm*—Arthur J. Plantamura; Birgit E. Morris

[57] ABSTRACT

Printing plates having a photoresist layer thereon that can be exposed by a computer controller laser have improved sensitivity and do not require a photomask step. We have found photoresists that include a film forming polymer, an organo azide and a photosensitive dye that absorbs light at the frequency of the patterning laser and converts it to heat energy. The heat energy in turn elevates the temperature of the organo azide above its dissociation temperature, destroying the azide in areas exposed to the light source, and solubilizing those regions. A post pattern exposure flood exposure with ultraviolet light hardens the unexposed resist, improving its resistance to etch solvents.

8 Claims, 1 Drawing Sheet

PHOTORESISTS AND METHOD FOR MAKING PRINTING PLATES

This invention relates to improved positive photopolymer formulations and to their use in preparing printing plates. More particularly, this invention relates to the use of organo-azide-containing photopolymer compositions for making printing plates.

BACKGROUND OF THE INVENTION

Photopolymers are used to make either positive-working or negative-working patterns on various substrates. Solvent-developable photopolymers are a particular class of photopolymers that have the ability to either become more soluble, or less soluble, when exposed to light of a particular wavelength. Positive photopolymers become more soluble, and negative photopolymers become less soluble in a developer solution. When exposed through a patterned mask, after development of the resist with a solvent, a like or opposite pattern of the resist remains on the substrate. This developed or patterned photopolymer layer can then be used to prevent the action of a corrosive liquid or etchant (or etch gas when plasma etching is employed) from reacting with and removing portions of the substrate not protected by the photopolymer.

Photopolymers, or resists, have long been used in the semiconductor industry directly on semiconductor wafers to etch various features into the substrate. Resists are also used to make printed circuit boards wherein a conductive metal is deposited in resist openings to form printed circuits on the board substrate.

In the printing plate art, resists are also used to form an image on a substrate, generally a metal plate. Ink is applied to the plate having a patterned resist layer thereon, and the ink can be transferred to another medium, such as paper. This process is well known.

Recently, an improved printing plate technique has been developed that uses a bimetal, usually copper clad aluminum, for the printing plate. In order to make this plate, a resist is applied over the copper, and exposed to light of a desired frequency. Generally the resist is covered with a patterned film emulsion or mask so that only certain areas of the resist are exposed, as shown in FIG. 1A, illustrating a dot pattern. The resist is hardened or cross linked by the light, the film emulsion or mask is removed, and the plate developed to solubilize the unexposed regions, as shown in FIG. 1B. The substrate is then etched, whereupon the copper layer not covered by resist is removed, as shown in FIG. 1C. Ink is applied to the copper remaining on the aluminum plate in a press, and thereafter transferred to another substrate. The inked image is shown in FIG. 1D.

With the coming of computer graphics and patterns available in digital form, the problems of direct conversion of such patterns and information to a printing plate are being addressed. This can be done using computer control of a laser light source to transfer the image information to a printing plate. A suitable laser scans across the plate, and the computer turns the laser on and off to pattern expose the resist. This eliminates the step of making a mask of the desired pattern, and, because the laser light can be finely controlled, an exact amount and frequency of light exposure of the resist and improved accuracy of the pattern can be obtained.

The resist for such a system is important. The resist exposed to light must change its solubility between the exposed and non-exposed regions; it must be developable with standard solvents; and the insoluble portions must be insoluble enough so that they remain insoluble for a time sufficient to ensure that the soluble portions are completely removed during development, but that at least some thickness of the insoluble portions of the resist remain after development. Further, a good resist for printing plates or other uses, such as for making printed circuit boards, must be able to withstand attack by the etch solution used to etch the exposed portions of the substrate. These requirements are not trivial.

Thus it would be highly desirable to obtain resist formulations that meet the requirements discussed above so that very exact pattern replication of images from a computer controlled laser directly to a metal substrate can be obtained.

SUMMARY OF THE INVENTION

We have found that excellent positive resists comprise organo azide compounds mixed with a suitable film-forming polymeric resin, and a dye sensitive to a desired region of the spectrum. These ingredients can be admixed with suitable organic solvents to make a resist composition that is sensitive to laser light. The laser light must be able to be converted to heat energy by the dye which is present in an amount sufficient to raise the temperature of the resist film above the decomposition temperature of the organo azide. The resist compositions of the invention can be patterned by direct application of computer controlled lasers to form finely controlled patterns.

Further, the unexposed resists cross link when flood exposed to ultraviolet (hereinafter UV) light, as from a UV lamp, which hardens the resist in areas not already exposed to the laser light. This improves the solubility contrast between exposed and non-exposed areas of the resist. This hardening has another advantage also, in that it provides improved etch resistance for the patterned resist.

The resists are useful to transfer patterns directly from a computer to a substrate such as a printing plate.

DETAILED DESCRIPTION OF THE INVENTION

Figure 1A:
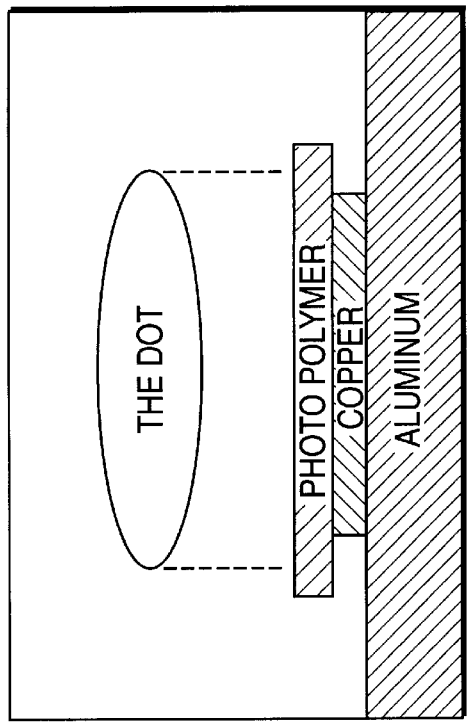
FIGS. 1A, 1B, 1C and 1D illustrate the steps used to expose and form a pattern on a bimetal printing plate according to the prior art.
Figure 1C:
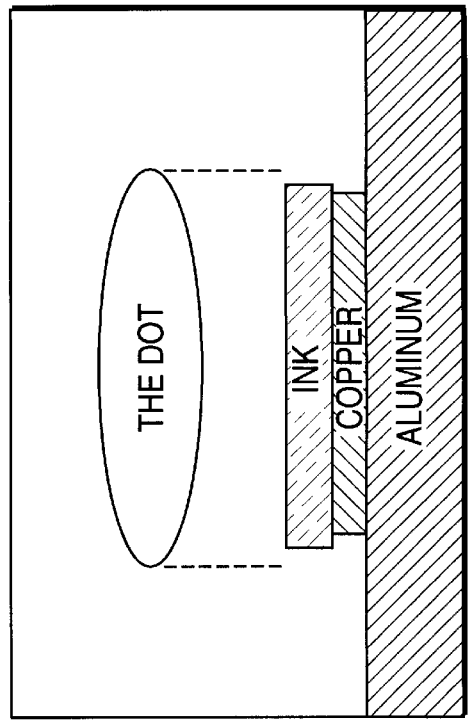
Figure 1B:
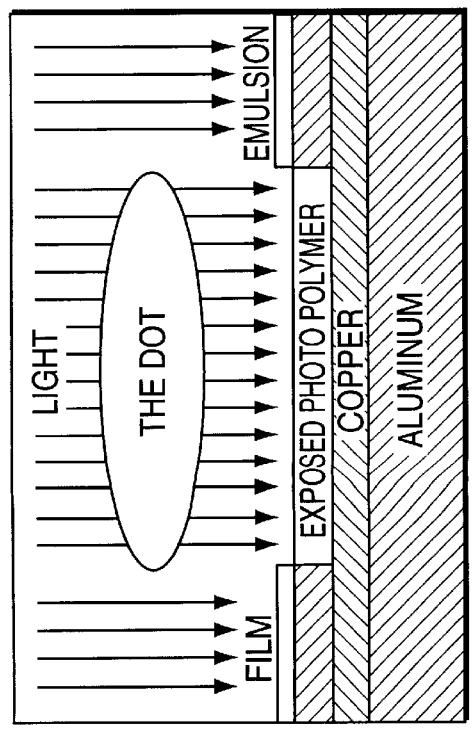
Figure 1D:
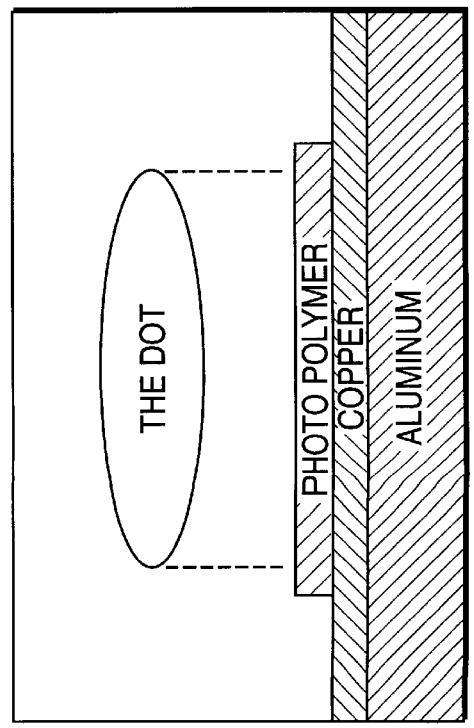

The positive resists of the invention include an organo azide compound mixed with a suitable polymeric resin and a dye that is sensitive to light of a particular laser, and that is also soluble in the resist solvent. Additional ingredients can be added, such as a pigment that can improve the contrast between the resist layer and an underlying substrate, and surfactants designed to adjust the texture of the resist so that it will form a smooth coating having a uniform thickness on a substrate. Typically lithographic resist films of this type have a dry thickness of about 0.5–2 micrometers. The above ingredients are then admixed with a suitable organic solvent so that it can be applied, as by spinning, as a thin film having a uniform thickness on the substrate. Generally the solids are dissolved to a total concentration of about 5% by weight in the mixed organic solvent.

Polymeric resins suitable for use herein include polyvinyl formal resin, and polymers and copolymers of acrylates and methacrylates, styrene and the like, Suitable organo azide compounds are well known in the literature and multifunctional, i.e., compounds having more than one azide group, have been disclosed as negative, or cross linkable, resists. However, monofunctional azides, which are not known to form cross linked negative resist patterns, are also suitable for use in the present invention. Suitable azides include monoaryl and vinyl azides, or bis arylazides, which may be substituted by various halogen and other radicals. Organoazides such as acidophthalic compounds that can form polymers are disclosed in U.S. Pat. No. 3,002,003 to Merrill et al for example. Cai et al, in Chem. Mater. 1994, Vol 6, pp 1822–1829 in an article entitled "Development of highly Efficient Deep-UV and Electron Beam Mediated Cross-Linkers: Synthesis and Photolysis of Bis (perfluorophenyl) Azides" made bis(perfluorophenyl) azides as negative resists for use with deep UV light and Electron-beam resists. Other azides are known and can be used herein.

These organoazides are used together with dyes that are photosensitive to the light emitted by the particular laser used for patterning the resist.

Although we do not wish to be bound by any particular theory, and the exact mechanism of the decomposition of the photopolymers is not known with certainty, it is presently believed that a high intensity laser light excites electrons in the dye absorbers so that the laser light is transformed into heat energy. This heat energy is transmitted to the organo azide compound, dissociating the compound, and making it soluble in developer solvents.

Thus the dye chosen for the present resists must be sensitive to the frequency of the laser used to expose the resist, and must be able to absorb the radiation from the laser and convert it to heat. Various dyes are well known and available commercially that are sensitive to infrared light for example, having various emission frequency ranges. Merocyanine, cyanine and tricarbocyanine dyes are readily available infrared absorbing dyes. At the present time, infrared lasers, such as diode lasers, YAG lasers, carbon dioxide lasers and the like are readily available. However, in future lasers may be developed that lase in the visible light ranges as well. What is important here is that the dye be sensitive in the same region of the spectrum as the light emitted by the laser pattern light source.

Since it is well known that multifunctional organo azides cross link in the presence of ultra violet light, a flood exposure to ultra violet light can be made after the pattern exposure by the laser. This flood exposure cross links the remaining organo azides in the resist, hardening the resist pattern. This cross linking reaction can also occur by heating the printing plate above about 150° C., e.g., to 160–180° C. However, since it takes more time to ramp the patterned resist coated printing plate to such temperatures and to cool the plate back to room temperature than to flood expose the printing plate with ultraviolet light, the flood exposure method is presently preferred.

Optionally, but preferably, a pigment can be dispersed in the resist solvent. A pigment can provide improved visual contrast between the resist film and the underlying substrate. This pigment may be insoluble, but must be dispersable in the resist solvent, and must be one that does not absorb light at the frequencies of the laser used to expose the resist. The pigment is added to provide additional contrast between the resist and the underlying substrate, so that it is more readily apparent when the development of the resist is complete.

Thus, in order to improve the insolubility of the insoluble portions of the resist after exposure to laser light, the resist can be subsequently flood exposed to ultra violet (hereinafter UV) light, as from a UV lamp source. The organo azides remaining on the printing plate cross link in the presence of UV light, thus decreasing their solubility and making them less permeable to developer solvent, and to etchants for the substrate. That portion of the organo azide that has already been exposed has been substantially dissociated by the laser light during the image-wise exposure.

The resist compositions are made by mixing the resin, the organo azide and the laser sensitive dye together, and dissolving in a suitable organic solvent. Generally the resist solution contains about 5% of solids. Additional ingredients can include surfactants, UV pigments as discussed above, coating agents and the like, as is known. For example fluorocarbon surfactants are known that are used in photoresists of various types.

The general process for making printing plates with the resists of the invention is detailed below.

A. The resist formulation is prepared and applied in known manner, as by spin coating, to a printing plate substrate. The preferred printing plates for use herein are copper clad aluminum plates. The resist may be dried if desired.

B. The resist covered plate is then image-wise exposed to a computer controlled high intensity light. The light source should deliver about 100–300 mJ/cm$^2$ of light to the resist layer in a short period of time. Preferably each region of the plate should be exposed by a flash of light of a few microseconds or less duration. A photomask can be applied over the resist layer if desired, but it is preferred to expose the resist layer by directly scanning with a computer controlled laser. Suitable lasers include lasers that emit light in the infrared region, such as diode lasers, YAG lasers, or $CO_2$ lasers and the like. But lasers that emit light in the visible region of the spectrum are also suitable when used with a dye that is able to convert light of that wavelength into heat energy. The laser light is absorbed by the resist which becomes more soluble in the resist developer in areas exposed to the laser light.

C. As an optional, but preferred step, the printing plate or other substrate is then flood exposed to UV light. The unexposed organo azide in the resist cross links in the presence of UV light, which makes the resist less soluble in resist developer, and hardens the portions of resist that have not been exposed to IR light. Thus the contrast in solubility between IR exposed and non-exposed resist areas is increased. This is advantageous because the latitude for resist development is increased, and the hardened resist portions are less soluble also in the substrate etchant. It is believed that flood exposure to the UV light acts to excite electrons in the organo azide, causing cross linking, as contrasted to the decomposition caused by exposure to IR light, for example.

D. The resist is then developed using conventional developer solutions and equipment. The developing solvent solubilizes the exposed regions of resist, and washes it away, as by spray washing. The presence of the pigment is advantageous here because it is easier to determine when the resist has been removed down to the substrate in the image exposed areas.

E. After developing, the exposed portions of the substrate are etched. For bimetal printing plates, the copper is etched down to the aluminum substrate in areas not covered by resist, transferring the pattern to the underlying substrate.

F. After etching, the remaining resist is stripped in known manner and the substrate washed and dried. The copper areas remaining on aluminum printing plate substrates will adsorb printing inks, which can be transferred to another medium, such as paper.

The invention will be further described in the following examples, but the invention is not meant to be limited to the details described therein. In the examples, parts and percentages are by weight unless otherwise noted.

EXAMPLE 1

Preparation of Butane diol di(4-azidotetrafluorobenzoate)

Pentafluorobenzoic acid (21.2 gm or 0.1 mol) and 4.5 gm or 0.05 mol of butane diol were added to a 250 ml round bottom flask and purged with nitrogen. A solution of 1,3-dicyclohexylcarbodiimide, 100 mls of a 1 molar solution in methylene chloride was added and stirred for 24 hours and filtered. The resulting liquid was cooled to 5° C. to produce a further precipitate, which was also removed by filtration. The solvent was evaporated from the solution to form a white crystalline solid having infrared (IR) and nuclear magnetic resonance (NMR) spectra consistent with the bis(pentafluorobenzoate) ester of butane diol, and was free from infrared peaks in the region of 2116 $cm^{-1}$ corresponding to the dicyclohexylcarbodiimide.

The compound was redissolved in acetone and 6.5 gm of sodium azide was added. This mixture was refluxed for 24 hours, filtered and the solvent evaporated to form a white solid. This solid was further purified by recrystallization from methanol. The resultant product had IR and NMR spectra consistent with the desired azide compound, including IR absorbance at 2132 $cm^{-1}$ (azide) and 1724 $cm^{-1}$ (ester carbonyl).

Preparation of Resist

Butane diol di(4-azidotetrafluorobenzoate) as prepared above was mixed with polyvinylformal and Projet 830 IR dye, an IR sensitive dye available from Zeneca Limited, varying the amount of the dye. A stock solution was prepared from the polyvinylformal in a mixture of 744 gm xylene, 396 gm dimethylacetamide and 0.296 grams FC-431, a fluorocarbon surfactant commercially available from 3M Company. The fluoroazide was added and finally the IR dye.

The formulations are summarized below, wherein PVF is polyvinyl formal:

| PVF, Parts | Fluoroazide | Projet 830 | Total Solids |
|---|---|---|---|
| 94.4 | 4.65 | .96 | 15.575 |
| 94.19 | 4.64 | 1.28 | 15.625 |
| 93.8 | 4.63 | 1.59 | 15.675 |
| 93.5 | 4.61 | 1.91 | 15.725 |

The coatings were spun at 60 rpm to form a resist film about 3.3 microns thick, and dried for 3 minutes at 110° C.

The plates were exposed using a diode laser and varying the amount of light, i.e., 150 $mJ/cm^2$, 200 $mJ/cm^2$, 300 $mJ.cm^2$ and 400 $mJ/cm^2$ to dot patterns varying from 3.1% to 96.9% patterns of dots about 10.6 microns in diameter.

The plates were developed using PDI developer 181D. Clear images were observed in all cases.

The plates were then etched with a copper etch, PDI's Q Etch™ solution. The plates were completely clean in the imaged areas and all copper was removed. There was no sign of attack in the non-imaged areas by the etchant.

The remaining resist was removed by conventional resist stripping solutions.

EXAMPLE 2

A resist formulation was prepared by mixing the following solids: 85.6 parts of polyvinyl formal resin; 5.2 parts of azido bis(2,6-benzylidine)cyclohexanone; 7.4 parts of Projet 830; 0.3 part of the surfactant FC-431; and 1.5 parts of phthalocyanine green pigment. The mixed solids were dissolved in a mixture of 66:33% of xylene and dimethylacetamide so as to make a 5% by weight solids solution, and coated on a copper clad aluminum bimetal printing substrate.

The printing plate was exposed using a computer controlled diode laser that emits light having a frequency of 830 nm at a dose of 150 $mJ/cm^2$, each laser flash delivered during a 3 microsecond period. The exposed plate was then flood exposed to UV light from a lamp.

The printing plate was then developed using PDI's 181D developer solvent, a solution available from Printing Developments, Inc (hereinafter PDI), in a spray developer system. The printing plate now had a patterned resist layer thereon wherein portions of the copper layer are exposed.

The exposed copper was then etched down to the aluminum layer using a copper etchant PDI's "Q Etch™", solution, a product of PDI.

Lastly, the remaining resist layer was stripped away with a suitable solvent, such as PDI's stencil remover solution.

EXAMPLE 3

The procedure of Example 2 was followed except varying the exposure of the resist to 150, 200, 300 and 400 $mJ/cm_2$. Comparable results were obtained.

EXAMPLE 4

Methyl 4-azidotetrafluorobenzoate was mixed with polyvinyl formal and Projet 830 IR dye as in Example 1. The coating solution was prepared by adding the azido benzoate to a suitable aliquot of the stock solution described in Example 1, such that the final solids contained 4.3% azidobenzoate, 2.0% Projet 830 and 92.7% of polyvinylformal.

The above resist composition was applied to a printing plate, exposed and developed as in Example 1. Excellent results were obtained.

EXAMPLE 5

A resist composition as described in Example 2 was applied to an aluminum substrate suitably treated to be hydrophilic as described for example in U.S. Pat. No. 3,181,461 to Fromson. The resulting polymer clad aluminum was exposed to high intensity laser light in a pattern, and developed as described in Example 3. Similar results were obtained.

EXAMPLE 6

The procedure of Example 2 was followed except using a copper clad steel substrate. The resultant plate was exposed and developed as in Example 2, and the exposed copper was removed using PDI's "265E" bimetal etchant. Finally the remaining photopolymer was removed. Excellent results were obtained.

EXAMPLE 7

A photopolymer composition was prepared as in Example 4 except using as the resin a copolymer of 50% benzyl methacrylate, 20% hydroxyethylmethacrylate, 20% methyl methacrylate and 10% allylmethacrylate prepared by solution polymerization of the corresponding monomers in 4-butyllactone at 55° C. for 24 hours, using azobis(2- methylpropionitrile) as an initiator at a concentration of 12%. The formulation was coated, exposed, developed, etched and stripped as in Example 1. Excellent results were obtained.

Although the present invention has been described in terms of particular embodiments, the invention is not meant to be limited to the details described herein. Substitution of other organo azides, laser light absorbing dyes, lasers or other high intensity light sources, surfactants, pigments and the like can be made without departing from the spirit of the invention. The invention is only to be limited by the scope of the appended claims.

We claim:

1. A printing plate substrate comprising a metal substrate having a layer thereon of a positive image producing formulation for use with computer exposed laser light pulses that emit light in the infrared region of the spectrum and deliver from about 100 to 400 mJ/cm$^2$ of light in a light pulse period and that is developable using a developer solvent to remove a portion of the light exposed photopolymer of the layer, the unexposed portion of the layer remaining on the substrate comprising
   a) a film forming polymeric resin;
   b) an organo azide compound, and
   c) an infrared absorbing dye, which has been exposed to infrared laser light pulses and treated by a developer solvent to form a pattern of exposed and unexposed regions on the plate.

2. A printing plate substrate according to claim 1 wherein said formulation additionally includes a fluorocarbon surfactant.

3. A printing plate substrate according to claim 1 wherein said formulation additionally includes a pigment that does not absorb light in the frequency range of the laser light.

4. A printing plate substrate according to claim 1 wherein said laser light delivery period is 3 microseconds or less.

5. A printing plate substrate according to claim 1 wherein said metal substrate is a copper clad metal plate.

6. A printing plate substrate comprising a metal substrate having a layer thereon of a positive image producing formulation for use with computer exposed laser light pulses that emit light in the infrared region of the spectrum and deliver from about 100 to 400 mJ/cm$^2$ of light in a light pulse period and that is developable with a developer solvent to remove laser light exposed polymer of the layer, said formulation comprising
   a) a film forming polymeric resin;
   b) an organo azide compound; and
   c) an infrared absorbing dye.

7. A printing plate substrate according to claim 6 wherein said metal substrate is a copper clad metal plate.

8. A printing plate substrate according to claim 6 that has been flood exposed to ultraviolet light.

* * * * *